US007966061B2

(12) United States Patent
Al-Abed et al.

(10) Patent No.: US 7,966,061 B2
(45) Date of Patent: Jun. 21, 2011

(54) PROCESSING AND ANALYZING PHYSIOLOGICAL SIGNALS TO DETECT A HEALTH CONDITION

(75) Inventors: Mohammad A. Al-Abed, Arlington, TX (US); Khosrow Behbehani, Arlington, TX (US); Michael T. Manry, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 959 days.

(21) Appl. No.: 11/846,919

(22) Filed: Aug. 29, 2007

(65) Prior Publication Data

US 2008/0058659 A1 Mar. 6, 2008

Related U.S. Application Data

(60) Provisional application No. 60/840,752, filed on Aug. 29, 2006.

(51) Int. Cl.
*A61B 5/0456* (2006.01)
(52) U.S. Cl. ........................................ 600/509
(58) Field of Classification Search ............... 600/508, 600/509, 521
See application file for complete search history.

(56) References Cited

U.S. PATENT DOCUMENTS

| | | | |
|---|---|---|---|
| 5,105,354 A | 4/1992 | Nishimura | |
| 5,902,250 A | 5/1999 | Verrier et al. | |
| 7,225,013 B2 * | 5/2007 | Geva et al. | 600/513 |
| 7,343,198 B2 | 3/2008 | Bebehani et al. | |
| 2003/0055348 A1 | 3/2003 | de Chazal et al. | |
| 2008/0269625 A1 * | 10/2008 | Halperin et al. | 600/508 |

OTHER PUBLICATIONS

MIDMARK Diagnostics Group, article on Brentwood IQ mark EZ Holter Window System, found at www.midmarkdiagnostics.com, and www.discountcardiology.com/catalog/brentwood_iqmark_ezholter_windows_systems.
Benitez D., P.A. Gaydecki, A. Zaidi, and A.P. Fitzpatrick, The use of the Hilbert transform in ECG signal analysis. Computers in Biology and Medicine. 31:399-406, (2001).
de Chazal P., et al., Automated Processing of the Single-Lead Electrocardiogram for the Detection of Obstructive Sleep Apnoea, IEEE Transactions on Biomedical Engineering, Jun. 2003, vol. 50, No. 6, pp. 686-696.
de Chazal P., et al., Automatic Sleep Apnoea Detection using Measures of Amplitude and Heart Rate Variability from the Electrocardiogram, Pattern Recognition, 2002. Proceedings. 16th International Conference on, vol. 1, pp. 775-778 (2002).

(Continued)

*Primary Examiner* — Eric D. Bertram
(74) *Attorney, Agent, or Firm* — Fulbright & Jaworski L.L.P.

(57) ABSTRACT

Described herein is a method of developing a fuzzy logic system to detect a non-normal health condition. In particular, signal processing and transformation of electrocardiogram (EKG) signals for sleep disorder breathing are provided. The method includes: recording EKG measurements during sleep; clipping the measurements into clips of a consistent length; calculating heart rate and obtaining an evenly sampled discrete time series data clip; performing Short-Time Discrete Fourier Transform on each data clip generating STDFT respective matrices; encoding each STDFT matrix into a grey-level image; calculating Grey-Level Co-occurrence Matrices; extracting textural features; performing statistical analysis on the features to formulate rules; and employing the rules in a Fuzzy Logic system. The system and method described herein yields an accuracy of 75.88%, or better, in detection of sleep apnea.

20 Claims, 6 Drawing Sheets

OTHER PUBLICATIONS

Hanly P. et al., Increased Mortality Associated with Cheyne-Stokes Respiration in Patients With Congestive Heart Failure. Am, J. Respir. Crit. Care Med., vol. 153, No, 1, Jan. 1996; 272-276.

Khalil M. M. and A. Rifaie. Electrocardiographic changes in obstructive sleep apnoea syndrome. Respiratory Medicine. 92:25-27 (1998).

Moody G.B., et al., Clinical Validation of the ECG-Derived Respiration Technique. Computers in Cardiology; 1987; 4; p. 507-10.

Moody G.B., et al., Derivation of Respiratory Signals from Multi-Lead ECGs. Computers in Cardiology; 1985; 2; p. 113-6.

Penzel T., J. McNames, P. de Chazal, B. Raymond, A. Murray, and G. Moody. Systematic comparison of different algorithms for apnoea detection based on electrocardiogram recordings. Medical and Biological Engineering and Computing. 40:402-407, (2002).

Quaranta A.J., et al., Cheyne-Stokes Respiration During Sleep in Congestive Heart Failure, Chest 1997; 111-2; 467-473.

Roche F., et al., Cardiac Interbeat Interval Increment for the Identification of Obstructive Sleep Apnea, PACE, vol. 25, No. 8, pp. 1192-1199, Aug. 2002.

Travaglini A, et al., Respiratory Signal Derived from Eight-iead ECG's,, in Computers in Cardiology. Piscataway, NJ: IEEE Computer Society Press, 1998, vol. 25, pp. 65-68.

Van Alste J.A., W. Van Eck, and O.E. Hermann, ECG baseline wander reduction using linear phase filterse, Computers and Biomedical Research. 19(5):417-427, (1986).

Young T., et al., Epidemiology of Obstructive Sleep Apnea. A Population Health Perspective. American Journal of Respiratory Critical Care Medicine, vol. 165. pp. 1217-1239, 2002.

Zywietz C., B. Widiger, and T. Penzel, Polysomnographic sleep recording with simultaneously acquired 12 lead ECGs: A study for detection and validation of apnea related ECG changes, Computers in Cardiology. 29:573-576, (2002).

Al-Abed, M., et al., A New Method to Detect Obstructive Sleep Apnea Using Fuzzy Classification of Time-Frequency Plots of the Heart Rate Variability, Conference Proceedings, 28th Annual International Conference of IEEE-EMBS, Volume Supplement, Aug. 30, 2006-Sep. 3, 2006, pp. 6493-6496.

Mendel, M., Chapter 5, Uncertain Rule-Based Fuzzy Logic Systems: Introduction and New Directions, Prentice Hall, NF, 2001.

* cited by examiner

PROCESSING AND ANALYZING PHYSIOLOGICAL SIGNALS TO DETECT A HEALTH CONDITION

CROSS-REFERENCES TO RELATED APPLICATIONS

This application claims the benefit of U.S. Provisional Application No. 60/840,752 filed Aug. 29, 2006.

BACKGROUND OF THE INVENTION

This invention relates generally to processing physiological signals and assessment of the processed signals to detect a health condition. As a specific example, a process and analysis for detecting sleep apnea from heart rate variability signals derived from electrocardiograms (EKG) signals is described.

Obstructive sleep apnea (OSA) is a significant health problem with health implications, ranging from excessive daytime drowsiness to serious cardiac arrhythmias. OSA, or intermittent cessation of breathing, is associated with increased risks of high blood pressure, myocardial infarction, and stroke. Sleep apnea is associated with increased mortality rates.

More particularly, OSA is conventionally defined as the total cessation of breathing during sleep for 10 seconds or more. This cessation is caused by an airway blockage in spite of a continuous respiratory nervous effort. This breath loss leads to a drop in blood oxygenation levels and sleep interruptions. Partial obstruction, Obstructive Sleep Hypopnea (OSH) is defined as the partial cessation (50% or more) of breathing during sleep for 10 seconds or more at a time.

Standard methods for detecting and quantifying sleep apnea and sleep disorders are based on respiration monitoring. Respiration monitoring is expensing and often disturbs or interferes with sleep, compounding the sleep problem. Further, evaluations for sleep breathing disorders, are typically done by specialists which are not accessible to a large portion of the population. The actual prevalence of sleep apnea is elusive.

A number of recent studies have eluded to the possibility of detecting sleep apnea using electrocardiograms (EKGs). EKG recordings are minimally intrusive and relatively inexpensive. Different research groups have concentrated on different features of the EKG overnight recordings. (de Chazel et al., IEEE Transactions on Biomedical Engineering, 2003, 50 (6), pp. 686-696; (Vijendra, Master's Thesis, Dept of Biomedical Engineering, University of Texas at Arlington, Arlington, Tex., USA, 2003; Penzel et al., Medical and Biological Engineering and Computing, 2002 40, pp. 402-407). Some groups concentrated on time-domain characteristics of the EKG signal, such as Angle of Mean Electrical Axis and Heart Rate Variability (HRV). Other groups looked at frequency-domain parameters such as PSD (Vijendra; Penzel et al.) and time-frequency plots (de Chazel et al.; Hilton et al., Medical and Biological Engineering and Computing, 1999, 37, pp. 760-769). However, time-frequency plots have only been studied in a qualitative manner, in which some noted differences between normal subjects and OSA patients have been described but never quantified or assessed for accuracy. Even with these limitations, the studies support the conclusion that HRV signals carry numerous measures that are sensitive to sleep disordered breathing, as well as other disorders influencing the cardiovascular system.

Thus, a method of processing, quantifying, and analyzing HRV signals, derived from EKGs, to detect apneic episodes is desirable. The accuracy of the method also needs to be established for clinical applications and other evaluations.

SUMMARY OF THE INVENTION

The present invention provides a method of processing, quantifying, and analyzing HRV signals, derived from EKGs, to detect apneic episodes.

The present invention provides a method of and means for developing a system to test patients for sleep apnea.

One aspect of the invention is a new method of processing time frequency plots of heart rate variability signals, derived from nocturnal EKGs, and outputting transformed data suitable for diagnostic evaluation.

Another aspect of the present invention is a new method of analyzing processed HRV signals to detect apneic episodes.

Another aspect of the present invention is a new method of analyzing processed HRV signals to classify a patient as normal or as suffering from OSA.

Another aspect of the present invention is to employ the new method of HRV signal processing and analysis to classify a patient as normal or as affected by cardiovascular dysfunction.

Those skilled in the art will further appreciate the above-noted features and advantages of the invention together with other important aspects thereof upon reading the detailed description that follows in conjunction with the drawings.

BRIEF DESCRIPTION OF THE DRAWINGS

For more complete understanding of the features and advantages of the present invention, reference is now made to a description of the invention along with accompanying figures, wherein.

DETAILED DESCRIPTION OF THE INVENTION

Although making and using various embodiments are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively.

Figure 1:
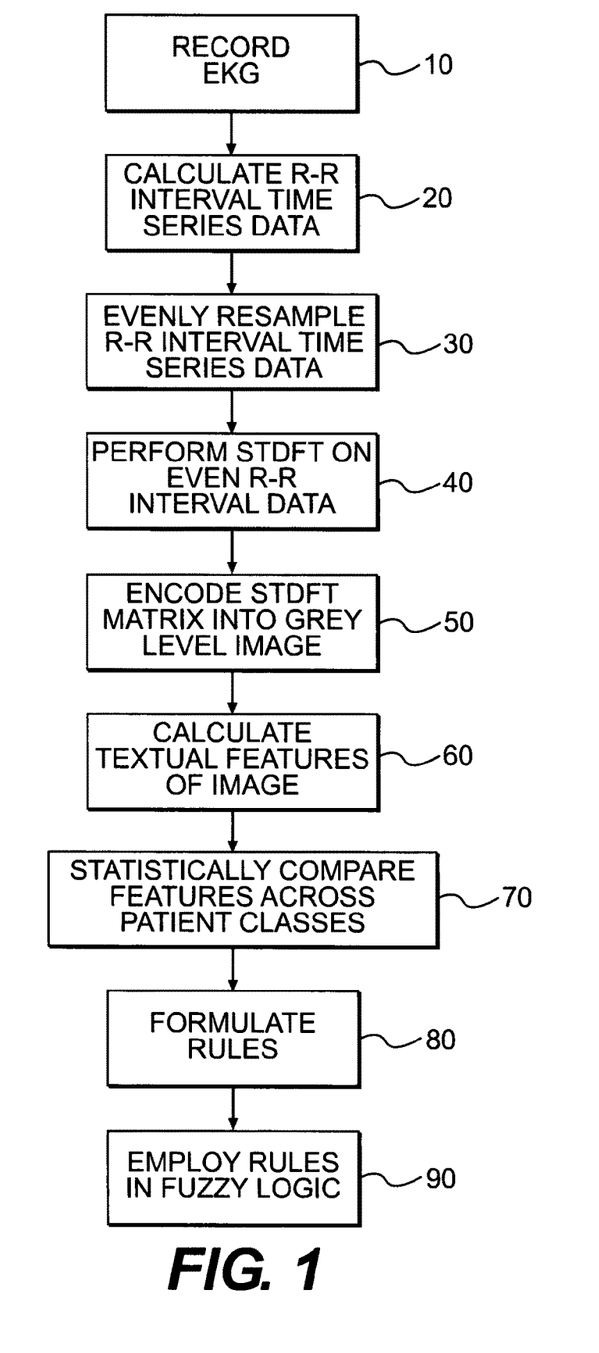
FIG. 1 depicts a block diagram of a method of signal processing according to an exemplary embodiment of the present invention.

An embodiment of a method of signal processing according to an exemplary embodiment of the present invention is shown in FIG. 1. EKG measurements are recorded during sleep. The measurements are clipped to 900 seconds 10. Lead I of each EKG signal clip is used to calculate the R-R interval, heart rate, the R-R Interval Discrete Time Series is calculated for each clip 20. The resultant time series is evenly resampled at 10 Hz using cubic spline interpolation 30. Short-Time Discrete Fourier Transform is performed on each 10 Hz sampled data clip generating STDFT respective matrices 40. Each STDFT matrix is encoded into a grey-level image 50. A set of nine textural features is calculated for each encoded image 60. Statistical analysis was performed on each of the nine features across the normal and OSA patient classes 70. Rules were formulated based on the statistical analysis and the independence of the features 80. Rules were employed in a Fuzzy Logic system in which the features of each clip were used as inputs 90.

Each of the steps illustrated in FIG. 1 will be described in greater detail with reference to a specific example. In this example, the data used to formulate and test the method of signal processing and analysis was previously collected and processed by Behbehani, et al. (Behbehani, et al., Conference Proceedings, 26th Annual International Conference of the IEEE EMBS 2004, pp. 3881-3884). Twelve (12) normal (NOR) subject patients were represented in this example. None of them had any known history of sleep disorder breathing, OSA, or otherwise. Fourteen (14) patients, previously diagnosed with OSA at an accredited sleep evaluation facility were also represented. During the mentioned study, a certified sleep expert, blind to the study, scored sleep disorder breathing events for all subjects, and apnea/hypopnea (OSA/OSH) events were qualitatively described.

EKG recordings were made on the 26 individuals, step 10 of FIG. 1 and divided into 900 second clips. Finding the R-peaks in the EKG signal defines a discrete time series from which heart rate can be calculated 20. The overall mean heart rate, R-peak detection error, for the acquired data (1.78 million beats) was 1% (S. Vijendra, Master's Thesis, Dept. of Biomedical Engineering, University of Texas at Arlington, Arlington, Tex., 2003). From the R-Peak detection, each R-peak can be associated with a single value that corresponds to the time interval between that peak and the peak before it. This clearly results in a discrete time series that is unevenly sampled. This time series is evenly resampled at 10 Hz with cubic spline interpolation 30, yielding a 9000-point heart rate variability (HRV) series.

There were 198 usable 900-second clips; 92 normal clips from NOR subjects and 106 event clips from OSA subjects.

Short-Time Discrete Fourier Transform (STDFT) was performed on the HRV equally-spaced discrete time series 40. A Hanning window was used with N=300, resulting in 9000 point in time and 1250 in frequency from 0 to 5 Hz. Since the study of Behbehani et al. showed the frequency range of 0 to 0.5 Hz to be the most promising, only the lower 125 rows of data were included in the STDFT Matrix. In order to decrease the computational load, without effecting the resolution, the resulting matrix is sampled at every n=4 points. The STDFT complex matrix is reduced to 2250 discrete temporal columns by 125 discrete frequency rows 40.

Each clip is now in the form of a 125×2250 point complex matrix. Each of the 198 complex matrices is then encoded into four different grey-scale images 50.

These matrices are handled as complex valued function of two variables i and j. This allows for conventional matrix processing methods to be applied, or for these matrices to be processed as pictorial images, after converting the complex values of the matrices to grey-level encoded values. Note, that color scale values could be used in an alternate embodiment.

It is this conversion that enables susbsequent classification (OSA identification in the present example) to be accurately performed on STDFT transformed data clips extracted from temporal signals. In the present example, the temporal signal is heart rate variability, derived from an EKG. However, the same conversion method can be applied to alternate EKG derivations and/or alternate physiological signals.

Four different grey-scale encoding methods, yielding 4 different images with different features were performed for each of the 198 clips. A first grey scale encoding method, Magnitude Encoding with 16 Grey Levels ($N_g=16$) is described as follows. For encoding purposes, the global maximum and minimum magnitude values of the entire matrix $I_{125 \times 2250}$ were found. The entire matrix was normalized with respect to $I(m,n)_{max}$. Then all values were quantized to 16 equally-spaced bins, with bin length defined as:

$$\frac{I(m, n)_{max} - I(m, n)_{min}}{16}. \tag{1}$$

The quantized 16-gray-level matrix, $I_{g16}(m,n)$, was found using the following rule:

$$\text{If } \left( \left[ i \times \frac{I(m, n)_{max} - I(m, n)_{min}}{16} \right] \leq I(m, n) < \left[ (i+1) \times \frac{I(m, n)_{max} - I(m, n)_{min}}{16} \right] \right) \Rightarrow I_{g16}(m, n) = i \tag{2}$$

$$\text{for } 0 \leq i \leq 15, \; 1 \leq m \leq 125, \; 1 \leq n \leq 2250.$$

A second grey-scale encoding method, Magnitude Encoding with 32 Gray levels ($N_g=32$) provides higher resolution and is described as follows. The entire matrix was normalized with respect to $I(m,n)_{max}$. Then all values were quantized to 32 equally-spaced bins, with bin length defined as:

$$\frac{I(m, n)_{max} - I(m, n)_{min}}{32}. \tag{3}$$

The quantized 32-gray-level matrix, $I_{g32}(m,n)$, was found using the following rule:

$$\text{If } \left( \left[ i \times \frac{I(m, n)_{max} - I(m, n)_{min}}{32} \right] \leq I(m, n) < \left[ (i+1) \times \frac{I(m, n)_{max} - I(m, n)_{min}}{32} \right] \right) \Rightarrow I_{g32}(m, n) = i \tag{4}$$

$$\text{for } 0 \leq i \leq 31, \; 1 \leq m \leq 125, \; 1 \leq n \leq 2250.$$

A third grey-scale encoding method, Ln(Magnitude) Encoding with 16 Gray levels ($N_g=16$) is very sensitive to the minimum and maximum values. Taking the natural logarithm of the magnitude of $I(m,n)$ will suppress the global maximum, and give rise to the details of the local maxima. The global maximum and minimum intensity values of the entire matrix $I_{125 \times 2250}$ were found. The entire matrix was normalized with respect to $I(m,n)_{max}$. Then all values were quantized to 16 equally-spaced bins, where each bin's length is equal to:

$$\frac{I(m, n)_{max} - I(m, n)_{min}}{16}. \tag{5}$$

The quantized 16-gray-level matrix, $I_{gLn16}(m,n)$, was found using the following rule:

$$\text{If}\left(\left[i \times \frac{I(m,n)_{max} - I(m,n)_{min}}{16}\right] \leq I(m,n) < \right. \quad (6)$$

$$\left.\left[(i+1) \times \frac{I(m,n)_{max} - I(m,n)_{min}}{16}\right]\right) \Rightarrow I_{gLn16}(m,n) = i$$

for $0 \leq i \leq 15$, $1 \leq m \leq 125$, $1 \leq n \leq 2250$.

A fourth grey-scale encoding method quantized the image into unequally spaced bins. The first, second, and third encoding methods used equal spaced gray-level bins. The images according to the fourth encoding method are based on quantizing the matrix into unequally spaced bins, where the length of the bin is inversely proportional to the histogramic distribution of the $I(m,n)$ magnitude values. In other words, the higher the occurrence of a certain range of values in the matrix $I(m,n)$ is, the smaller the bin size that will contain them.

Figure 2:
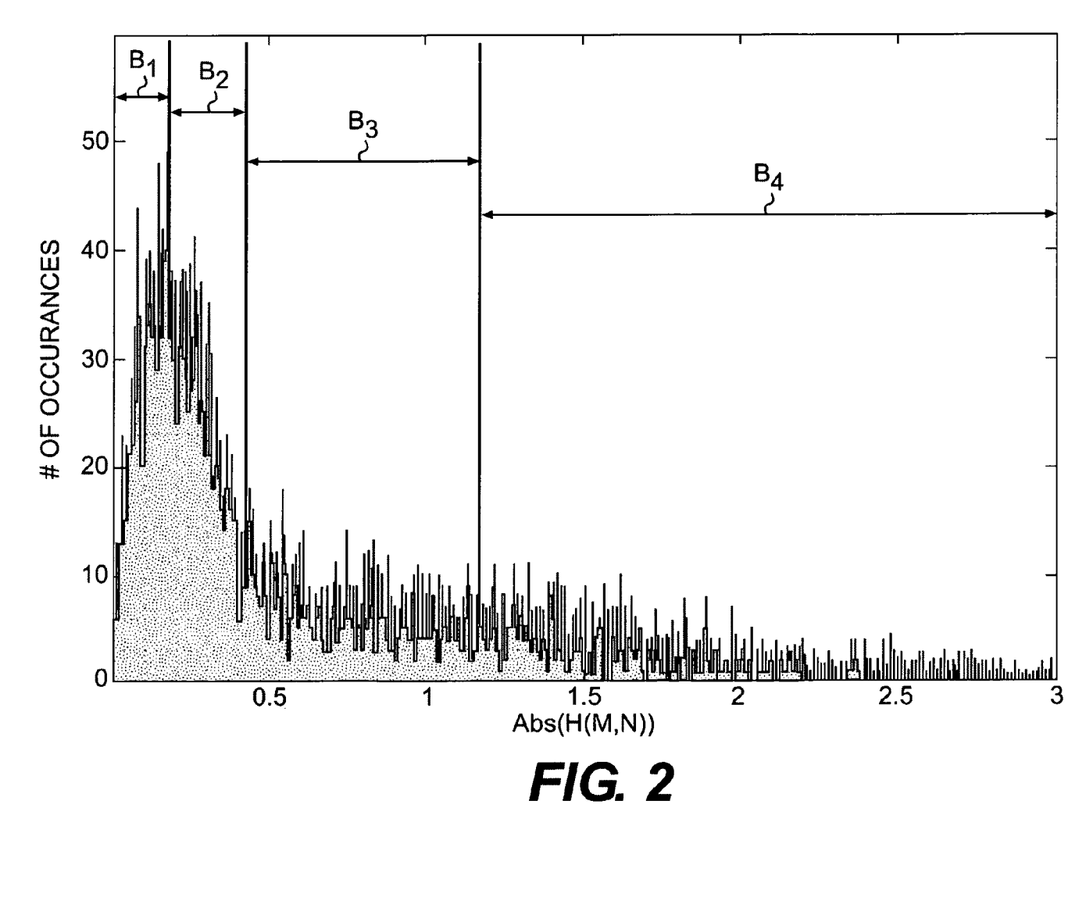
FIG. 2 shows the binning according to an exemplary encoding method of a histogram distribution of intensity values.

Hence, values with similar characteristics with be grouped together, and the effect of extremely high or extremely low values will be nullified. This means that all Ng grey levels will have equal distribution in the image. FIG. 2 illustrates the binning process with this encoding scheme for an example of four gray scales, Ng=4. The unequal bin lengths, B1, B2, B3, and B4 are due to the unequal intensity distribution 210, which is a function of the image itself. The histogram of the absolute matrix values clearly shows lower intensities occur more frequently.

No normalization is required for this Histogram Binning encoding method. Bin thresholds may be chosen so that ratio of value occurrences within the bin to the overall value occurrences for all bins is fixed. This value is equal to $$\frac{1}{N_g},$$

and for $N_g=16$, for example, this value is 0.0625.

The quantized 16-gray-level matrix, $I_{gHist16}(m,n)$, was found using the following rule: If($I(m,n) \subset $ bin#i)$\Rightarrow I_{gHist16}(m,n)=i$, for $0 \leq i \leq 15$, $1 \leq m \leq 125$, $1 \leq n \leq 2250$.

An example intensity image histogram is shown in FIG. 2. Choosing $N_g=4$, the values falling within bin $B_1$ will have a quantized value of i=0 (Black). The values falling within bin $B_2$ will have a quantized value of i=1, which corresponds to a 66%-Gray shade. The values falling within bin $B_3$ will have a quantized value of i=2 (33%-Gray), and finally the trailing tail of intensity values falling within bin $B_4$ will have a quantized value of i=3 (White).

Figure 3A:
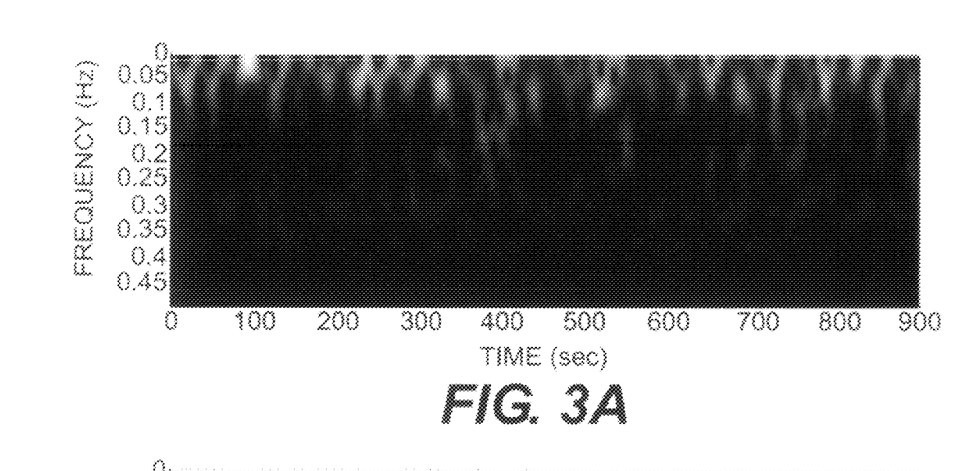
FIGS. 3A-D depict exemplary encoded images of the same clip, each image encoded by one of four different respective encoding methods.
Figure 3B:
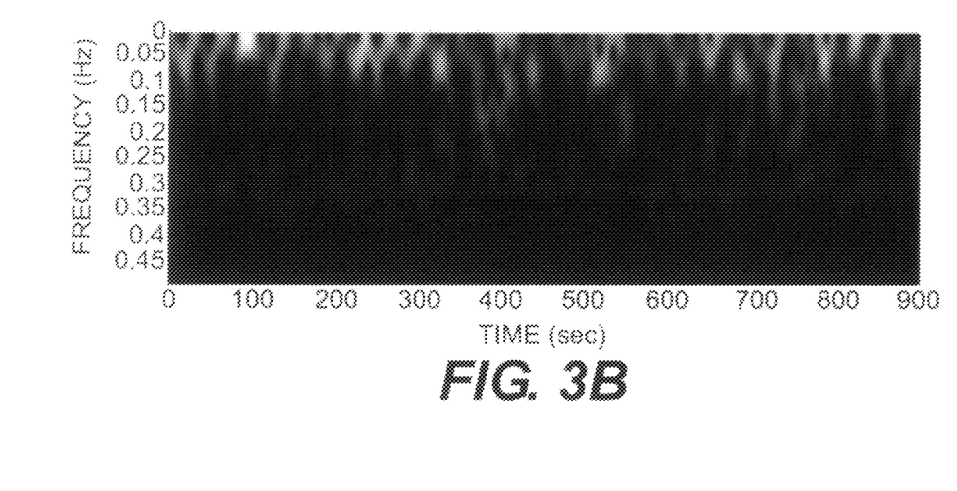

FIGS. 3A-D depict exemplary encoded images of the same clip, each image encoded by one of the four different encoding methods described above. FIG. 3A shows the encoded image of the complex STDFT matrix of clip 1 from subject NOR(1), using Magnitude Encoding with 16 Grey Levels ($N_g=16$). FIG. 3B shows the encoded image of the same complex STDFT matrix of clip 1 from subject NOR(1), using Magnitude Encoding with 32 Grey Levels ($N_g=32$).

Figure 3C:
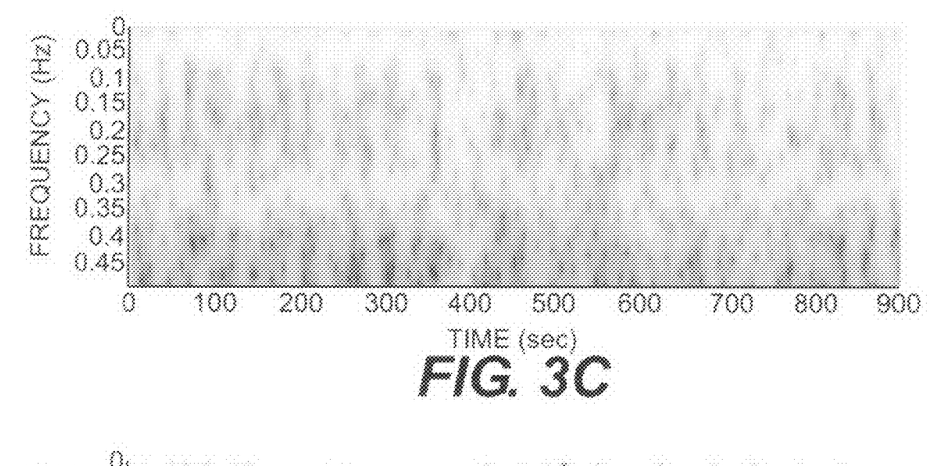
Figure 3D:
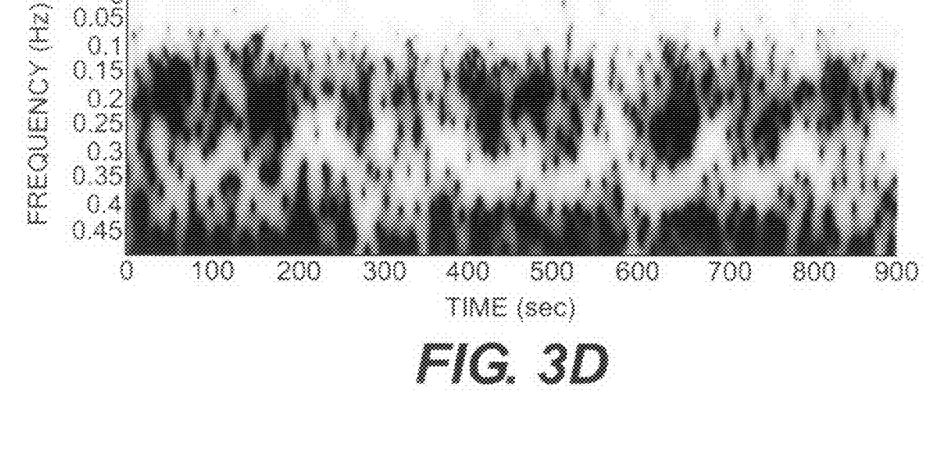
Figure 4A:
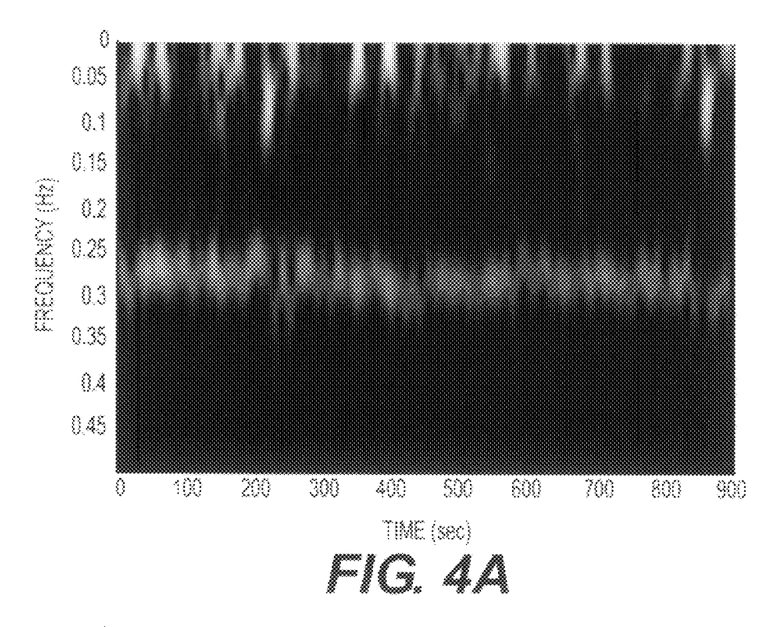
FIGS. 4A-B depict a 16 grey scale-image from a normal (NOR) and an OSA patient, respectively encoded using the same exemplary method in accordance with the present invention.
Figure 4B:
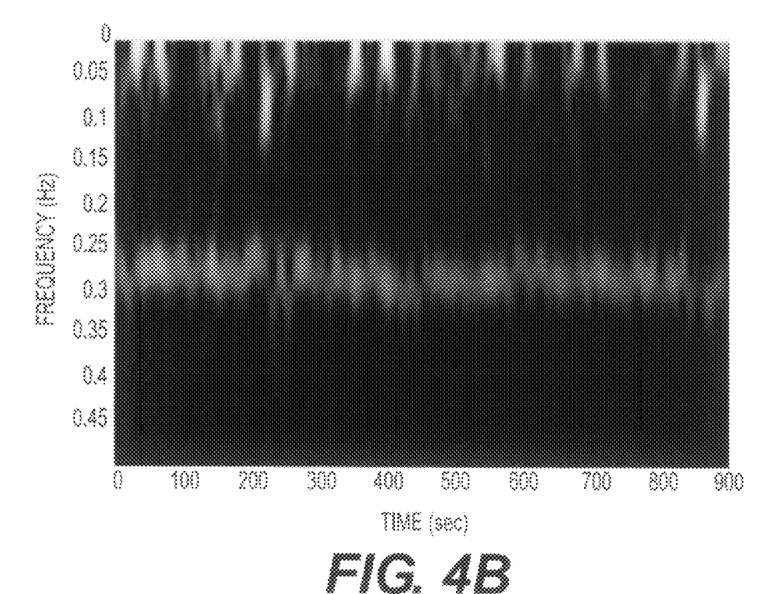

FIG. 3C shows the encoded image of the same complex STDFT matrix of the same clip 1 from subject NOR(1), using Ln(Magnitude) Encoding with 16 Gray levels ($N_g=16$). And FIG. 3D shows the encoded image of the STDFT matrix, also from normal subject 1, clip 1 of 198.

At this point in the signal processing process, there are 4×198 images, four images for each clip 50, shown in FIG. 1. Each one of a respective four images encoded by applying a different grey-level encoding method to the STDFT complex matrix.

Armed with these image sets, the process of analyzing the images and classifying the images, for example NOR or OSA, based on statistical properties of the images is described. Textural features for these images will be calculated for subsequent statistical analysis (Haralick et al., IEEE Transactions on Systems, Man, and Cybernetics 1972, 3 (6), pp. 610-619).

Gray Level Co-occurrence Matrices (GLCM) are Ng×Ng symmetric matrices that contain the count of paired i and j gray levels separated by a certain distance, d, and angle, θ (Haralick et al). From these counts, GLCMs, textural features are calculated 60, as shown in FIG. 1. GLCMs were originally developed to sort the massive number of satellite images in the early 1970's (Haralick et al).

For images with square pixels, there are four conventional values for θ that dictate the neighborhood relationship of any two paired pixels, 0°, 45°, 90°, and 135°. A single image can produce numerous different GLCMs, depending on the choice of parameters, d and θ. Parameter d, distance, is measured in pixel count, for example 3 pixels to the left is 3 pixels in the 0° direction.

Calculating GLCMs imposes a high computational load. In the example of four images for each of the 198 clips, each image was segment into 18 square manageable segments of 125×125 pixels (where 18×125=2250, the original image size). At 125 pixels, each segment represents 50 seconds in length. Two half segments, 64×125, were made for the lower frequencies which contained high power densities. The last segment of each 18 segments per image was discarded. All 17 125×125 segments coming from one image clip will be converted into a GLCM separately, and their results will be averaged to give a mean value GLCM for that one image. Similarly GLCMs of the two half segments will be averaged to yield a mean GLCM for that one image.

Normalized GLCMs (NGLCM) are GLCMs normalized to the total number of counted pairs, $N_p$. $N_p$ is function of image size, the orientation θ, and the distance d. For an image with size $I_p \times I_p$ pixels, $N_p$ is given according to the equations below.

$$N_p = 2 \cdot (I_p \times (I_p - d)) \text{ for } \theta = 0° \text{ and } 90°, \text{ and}$$

$$N_p = 2 \cdot ((I_p - d) \times (I_p - d)) \text{ for } \theta = 45° \text{ and } 135°.$$

Some NGLCMs are used in the example of 198 clips.

Still referring to the exemplary embodiment of 198 useable clips, a total 10 mean value GLCMs were calculated per clip. The distribution of 10 mean GLCMs was not uniformly distributed across the four grey scale images for each clip. The mean value GLCM distribution across images and corresponding parameters, d and θ, are summarized below.

For images constructed using Magnitude Encoding with 16 Grey Levels ($N_g=16$), shown for example in FIG. 3A, the following mean GLCMs were calculated:

| | |
|---|---|
| GLCM-1(125×125,$d=5$,θ=90°); | a. |
| GLCM-2(125×125,$d=1$,θ=90°); | b. |
| GLCM-3(64×125,$d=5$,θ=90°); and | c. |
| GLCM-4(125×125,$d=5$,θ=0°). | d. |

For images constructed using Magnitude Encoding with 32 Grey Levels ($N_g=32$), shown for example in FIG. 3B, the following mean GLCMs were calculated:

| | |
|---|---|
| NGLCM-5(125×125,$d=5$,θ=90°); | e. |
| NGLCM-6(125×125,$d=3$,θ=90°); and | f. |
| NGLCM-7(125×125,$d=1$,θ=90°). | g. |

For images constructed using Ln(Magnitude) Encoding with 16 Gray levels ($N_g=16$), shown for example in FIG. 3C, the following mean GLCMs were calculated:

NGLCM-8(125×125,$d$=5,$\theta$=90°); and　　　　h.

NGLCM-9(64×125,$d$=5,$\theta$=90°).　　　　i.

For images constructed using Histogram Binning ($N_g=16$), shown for example in FIG. 3D, the following mean GLCM was calculated:

NGLCM-10(125×125,$d$=5,$\theta$=90°).　　　　j.

For the example comprising 198 clips, nine Textural features were calculated from the GLCMs (Haralick et al). For all the subsequent measures, the following definitions are applicable: M(i,j) is the i, j element of the grey level co-occurrence matrix. Since M is symmetric, M(i,j)=M(j,i). $N_g$ is the number of grey levels used in the image.

$$\text{Matrix Mean is } \mu = \sum_i^{N_g} i \sum_j^{N_g} M(i,j). \qquad (7)$$

$$\text{Matrix Variance is } \sigma^2 = \sum_i^{N_g} (i-\mu)^2 \sum_j^{N_g} M(i,j). \qquad (8)$$

The nine Textural features are defined and calculated as provided below.

$$\text{Entropy (ENT): } ENT = -\sum_i^{N_g}\sum_j^{N_g} M(i,j) \cdot \log(M(i,j)). \qquad (9)$$

$$\text{Angular Second Moment (ASM): } ASM = \sum_i^{N_g}\sum_j^{N_g} [M(i,j)]^2. \qquad (10)$$

$$\text{Contrast: } CON = \sum_i^{N_g}\sum_j^{N_g} M(i,j) \cdot (i-j)^2. \qquad (11)$$

$$\text{Correlation (COR): } COR = \sum_i^{N_g}\sum_j^{N_g} \frac{M(i,j) \cdot (i-\mu) \cdot (j-\mu)}{\sigma^2}. \qquad (12)$$

$$\text{Dissimilarity (DIS): } DIS = \sum_i^{N_g}\sum_j^{N_g} M(i,j) \cdot |i-j|. \qquad (13)$$

$$\text{Inverse difference (IND): } IND = \sum_i^{N_g}\sum_j^{N_g} \frac{M(i,j)}{1+(i-j)}. \qquad (14)$$

$$\text{Inverse Difference Moment (IDM): } IDM = \sum_i^{N_g}\sum_j^{N_g} \frac{M(i,j)}{1+(i,j)^2}. \qquad (15)$$

$$\text{Variance (VAR): } VAR = \sum_i^{N_g}\sum_j^{N_g} M(i,j) \cdot (i-\mu)^2. \qquad (16)$$

$$\text{Inverse Recursivity (INR):} \qquad (17)$$

$$INR = -\sum_i^{N_g}\sum_{j=i+1}^{N_g} 2 \cdot M(i,j) \cdot \log(2 \cdot M(i,j)) - \sum_i^{N_g} M(i,i) \cdot \log(M(i,i)).$$

Figure 5:
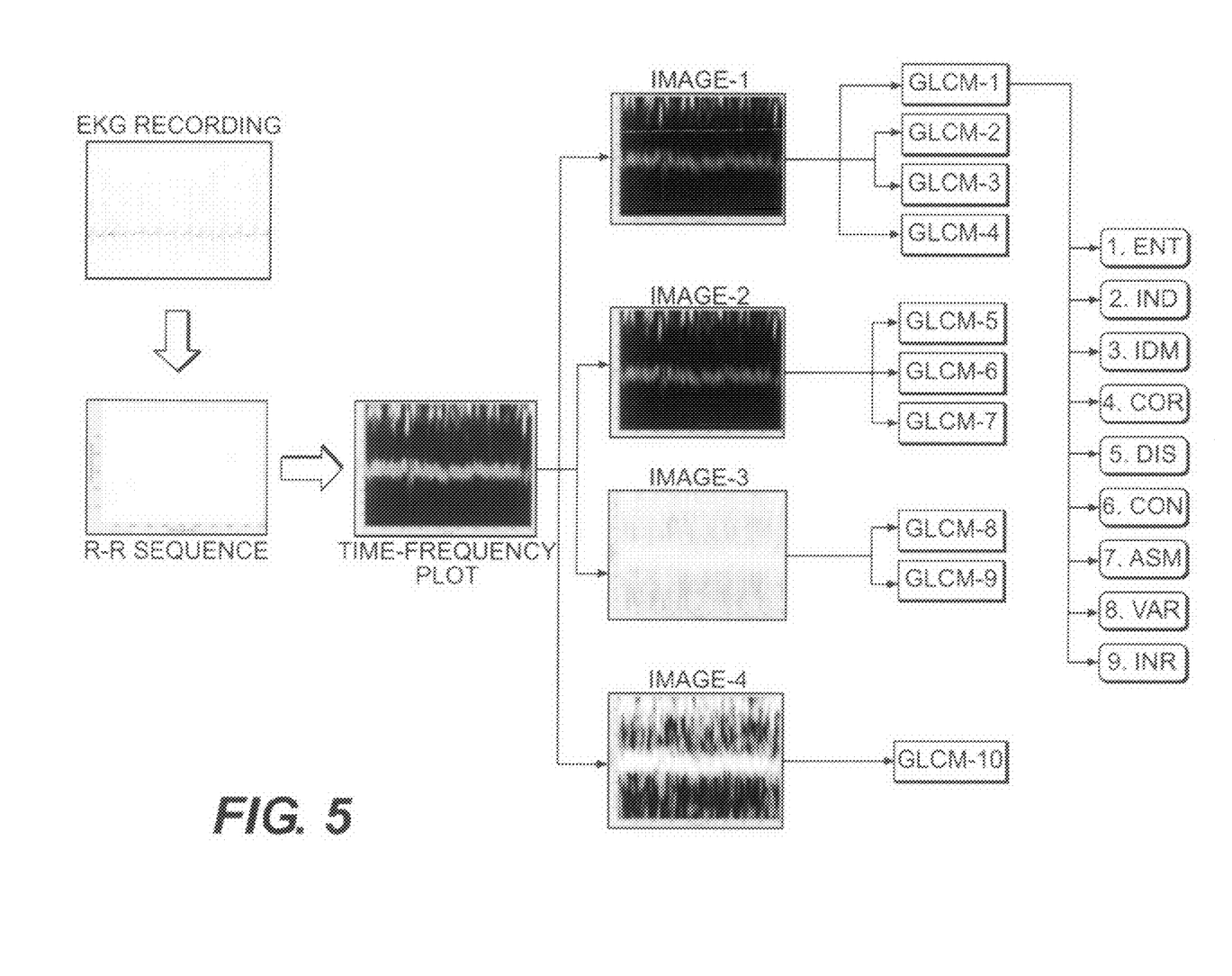
FIG. 5 is a flow chart representation of the signal processing from an EKG signal through feature extraction in accordance with an embodiment of the present invention.

A total of 90 average features is calculated for each of the 198 clips, 9 for each of the 10 GLCMs. Feature selection to enable discrimination between a first and second class, NOR and OSA, is evaluated using statistical analysis of the features 70, as shown in FIG. 1. Suitable Textural feature selection can be based on, for example, a gap between means with corresponding small standard deviations. In the particular example of 198 clips, features with a good first degree separation, large mean gap between NOR and OSA and small spread about respective means, were chosen as the features for class discrimination (NOR or OSA) 80, as shown in FIG. 1. Such features can, for example, be identified by a minimum deviation-to-mean ratio. FIG. 5 illustrates the signal processing steps on an EKG clip, according to the example of 198 clips. The number of clips, the number of encoded images (four shown), and the number of GLCMs, normalized or not, can vary in alternate embodiments consistent with the present invention.

Fuzzy logic systems have been used in previous studies to distinguish, classify, between inputs with overlapping input values (J. M. Mendel, "Uncertain Rule-Based Fuzzy Logic Systems: Introduction and New Directions", Prentice Hall, N.J., 2001). Membership functions (MFs), used in fuzzy logic systems, assign a membership degree between 0 (low) and 1 (high) to the range of inputs. Sigmoid MFs were chosen for the example of 198 clips, where, a sigmoidal function can be written as:

$$\mu_x(x) = 1/1 e^{-a(c-x)} \qquad (18).$$

In the exemplary embodiment of 198 clips, a singleton fuzzy system was employed. The system is made up of input fuzzifier, rule-fed inference engine, and a defuzzifier. The values of the selected features are used as inputs. Each value is given two membership degrees (MDs); NOR and OSA. The MDs are allocated using the sigmoidal MFs defined above. Initial $c_L$ and $c_H$ values are set to the means of lower and higher NOR and OSA means, respectively. Initial $a_L$ and $a_H$ values are set to 1. These MD values are then trained to find best fitting MFs that give optimum classification results.

Exemplary formulation of fuzzy rules is described in reference to Table 1, which summarizes statistical means of a given NGLCM, for correlation, inverse difference, and inverse difference momentum.

TABLE 1

|  | COR | IND | IDM |
|---|---|---|---|
| NOR | 0.835 | 0.923 | 0.997 |
| OSA | 0.891 | 0.947 | 0.993 |

With the example as shown in TABLE 1, there are $2^3=8$ fuzzy rules. Example fuzzy rules based on TABLE 1 would include: (a) IF COR is low AND IND is low AND IDM is high THEN clip is NOR; and (b) IF COR is high AND IND is high AND IDM is low THEN clip is OSA. Because all selected features are exclusively disjoint, in which each feature independently describes the image, rule reduction may be applied. The additional 2×3=6 rules useful with the inference engine for classifying NGLCM-X include: (a) IF COR is low THEN clip is NOR; (b) IF COR is high THEN clip is OSA; (c) IF IND is low THEN clip is NOR; (d) IF IND is high THEN clip is OSA; (e) IF IDM is high THEN clip is NOR; (f) IF IDM is low THEN clip is OSA.

For deffuzification, height defuzzification was used. A value of "1" was assigned to OSA clip diagnosis and "−1" to NOR clip diagnosis. A crisp decision boundary was set at "0."

In the exemplary embodiment of 198 clips, each fuzzy logic system (FLS) was recursively trained, using described methods known to one of ordinary skill (such as that described by Mendel (2001) in "Uncertain Rule-based Fuzzy Logic Systems: Introduction and New Direction," Prentice Hall, N.J.).

Using the statistical significant difference between NOR and OSA extracted textural features as a feature selection method, it was found that for the NGLCMs of TABLE 1, textural features COR, IND, and IDM showed significant differences and had a lowest spread to mean ratio. These features were inputs to a fuzzy logic system (FLS) layer. Each FLS was trained with the corresponding 3 features from each NGLCM. In other words, FLS-1 was trained using features $COR_1$, $IND_1$, and $IDM_1$, and so on through FLS-10, being trained using $COR_{10}$, $IND_{10}$, and $IDM_{10}$.

In an iteration, 92 NOR clips and 106 OSA clips were randomly divided into training set and matching set: 132 clips for training and 66 for testing. Mean of the training set was used as initial values for $c_L$ and $c_H$. The set was classified and output of FLSs were acquired and combined using weighed majority rule, as shown TABLE 2.

After training, data were combined using weighed majority rule to find a classification for each clip. TABLE 2 shows a representative example of such data for 6 randomly chosen clips, including classification and final decision. NOR clips are marked as (−1) and OSA are marked as (1). Each FLS corresponds to the texture values from a given GLCM, recall there are 10 GLCMs per clip in the 198 clip example.

TABLE 2

| | Clip No. | | | | | |
|---|---|---|---|---|---|---|
| | 1 | 2 | 3 | 4 | 5 | 6 |
| FLS-1 | −1 | 1 | 1 | 1 | −1 | 1 |
| FLS-2 | −1 | 1 | 1 | 1 | 1 | 1 |
| FLS-3 | −1 | 1 | 1 | 1 | 1 | −1 |
| FLS-4 | 1 | 1 | 1 | 1 | 1 | 1 |
| FLS-5 | −1 | −1 | −1 | 1 | 1 | −1 |
| FLS-6 | −1 | 1 | 1 | 1 | 1 | −1 |
| FLS-7 | −1 | 1 | 1 | 1 | 1 | 1 |
| FLS-8 | −1 | 1 | −1 | 1 | −1 | −1 |
| FLS-9 | −1 | 1 | 1 | 1 | 1 | −1 |
| FLS-10 | −1 | 1 | 1 | 1 | 1 | −1 |
| Majority Rule | −1 | 1 | 1 | 1 | 1 | −1 |
| Clip Diagnosis | −1 | −1 | 1 | 1 | 1 | −1 |

Performance of training and testing are evaluated by sensitivity, specificity and accuracy, which are calculated by the equations below.

$$\text{Sensitivity} = \frac{OSA_c}{\text{Total } OSA \text{ clips tested}} \times 100\%. \quad (19)$$

$$\text{Specificity} = \frac{NOR_c}{\text{Total } NOR \text{ clips tested}} \times 100\%. \quad (20)$$

$$\text{Accuracy} = \frac{OSA_c + NOR_c}{\text{Total } NOR \& OSA \text{ clips tested}} \times 100\%. \quad (21)$$

In equations (19) to (21), $OSA_c$ is the number of correctly detected OSA clips and $NOR_c$ is the number of correctly detected NOR clips.

A summary of sensitivity, specificity and accuracy for the training set and testing set in the example of 198 clips is depicted in TABLE 3.

TABLE 3

| | Training | Testing |
|---|---|---|
| Sensitivity | 86.87% | 83.22% |
| Specificity | 71.72% | 68.54% |
| Accuracy | 79.29% | 75.88% |

As can be seen from the results in TABLE 3, the system in accordance with this invention has good sensitivity. In the methods in accordance with the present invention of a combination of time and frequency domains in one plot (e.g., image) are used to quantitatively analyze signal recording, the analysis relying on a classification scheme described herein. Image processing and pattern recognition schemes and classifiers improve not only the detection rate of one or more particular signals, but are also reliable, effective, and efficient. The methods in accordance with this invention compare well to alternative conventional temporal or spectral methods being practiced.

A second classifier system can be developed according to the present invention. For example, in accordance with another exemplary embodiment, a Multilayer Perceptron network (MLP) is employed. An MLP is a form of a feed-forward neural network (NN). A feed-forward NN is does not have any of its frontward layer outputs feeding back into a previous layer's input. MLPs have been shown to be successfully employed in image classifier applications.

In an exemplary embodiment of the present invention, a three layer MLP was used, which has an input layer, hidden layer and an output layer. The input layer has a number of neurons (nodes) equal to the input vector length. The output layer consists of one neuron, accounting for a possibility of only 2 classes to be classified. The number of units in the hidden layer ($N_h$) is adjustable and effects classification accuracy.

Besides changing the number of hidden units, each layer of a MLP has two parameters that are trained to achieve maximum detection: node transfer function and weight vector. Both input and output layers use linear transfer functions (TF) for each neuron. This is achieved using MATLAB's linear TF purelin; MATLAB is a programming language by The Math-Works, Inc., (The MathWorks, Inc., Natick, Mass., U.S.A). The hidden layer, on the other hand, uses a hyperbolic tangent sigmoid function. MATLAB's implementation of this TF is:

$$f(n) = \frac{2}{(1 + e^{-2n}) - 1},$$

and the built-in TF is tansig.

A MLP can be created, for example, using the newff function in the Neural Network toolbox in MATLAB, The results of two MLPs that were developed to classify the clips based on two different sets of inputs drawn from the nine features and 10 GLCMs, described above are describe below. All GLCMs are normalized (NGLCM) for the MLP classifier system.

Training of a MLP, in accordance with this invention is achieved by fitting the network parameters to the desired output using BP. This step is analogous to the training of the FLS. The accuracy of the MLP system is not directly correlated to the number of training epochs, rather after an optimum $N_{ep}$, the accuracy of the system may actually decline with additional training epochs.

Using a selected feature set, used as input vectors to the MLP, the 198 clips are randomly assigned into two groups; training and testing, with a 2:1 ratio. With total of 198 clips, this is translated to 132 clips for training, and the remaining 66 for testing and validation. Then, the optimum number of hidden units ($N_h$) and training epochs ($N_{ep}$) are found as a pair using the method further described below.

For each possible $N_h$, the network is trained using the training set with a given number of epochs, $N_{ep}$, and then the weights and biases parameters of the network are fixed in order to run the test set and calculate the testing accuracy of the network. Once accuracies are stored for a first given $N_{ep}$, the MLP is then trained for the next $N_{ep}$ increment. The number of $N_{ep}$s ranged from 200 to 5000 in accordance with this invention. This allows for studying the average performance of the MLP at that given $N_h$. The one-step-secant back propagation method was used for training the MLP. Optimum pairs for of hidden units $N_h$ and training epochs $N_{ep}$ are determined from accuracy calculations in a 50-run Monte Carlo simulation. Once these pairs are chosen for each of the two MLPs at hand, 1000-run Monte-Carlo simulations are performed to study the performance of the detector MLPs. Tables 4 and 5 show the accuracies calculated during the optimization process, finding the best $N_h$, $N_{ep}$ pair.

The table below summarizes the accuracies of $N_{eps}$ for a given $N_h$.

TABLE 4

Testing Accuracy mean and standard deviation (std) for 50-run Monte-Carlo Simulation

| Validation | | Number of Training Epochs $N_{ep}$ | | | | | | | | | | | |
|---|---|---|---|---|---|---|---|---|---|---|---|---|---|
| $N_h$ | Accuracy | 200 | 600 | 1000 | 1400 | 1800 | 2200 | 2600 | 3000 | 3400 | 3800 | 4200 | 4600 | 5000 |
| 2 | Mean | 78.91 | 79.55 | 78.73 | 77.91 | 77.94 | 77.64 | 77.24 | 77.15 | 76.94 | 76.79 | 76.64 | 76.36 | 76.64 |
|   | Std  | 3.91 | 4.33 | 4.58 | 4.34 | 4.04 | 3.83 | 4.08 | 3.92 | 4.11 | 4.12 | 4.51 | 4.29 | 4.20 |
| 4 | Mean | 78.61 | 78.18 | 77.70 | 77.24 | 76.97 | 76.58 | 76.45 | 76.09 | 76.12 | 75.97 | 76.09 | 76.06 | 75.94 |
|   | Std  | 4.36 | 4.36 | 4.52 | 4.36 | 4.49 | 4.12 | 3.86 | 3.80 | 3.74 | 3.82 | 3.85 | 3.75 | 3.47 |
| 6 | Mean | 78.24 | 77.39 | 77.21 | 76.52 | 76.33 | 75.85 | 75.67 | 75.79 | 75.36 | 75.21 | 75.18 | 75.21 | 75.24 |
|   | Std  | 3.93 | 5.07 | 5.08 | 4.82 | 4.40 | 3.97 | 4.19 | 3.96 | 3.68 | 3.70 | 3.54 | 3.47 | 3.53 |
| 8 | Mean | 77.73 | 77.21 | 77.00 | 76.45 | 75.52 | 74.70 | 74.64 | 74.42 | 74.39 | 74.42 | 74.24 | 74.18 | 74.33 |
|   | Std  | 4.11 | 4.26 | 4.00 | 3.90 | 3.70 | 3.78 | 3.70 | 3.57 | 3.76 | 3.58 | 3.45 | 3.24 | 3.13 |
| 10 | Mean | 78.18 | 78.82 | 77.73 | 77.06 | 76.55 | 76.45 | 75.91 | 75.64 | 75.48 | 75.61 | 75.30 | 75.24 | 75.21 |
|   | Std  | 4.54 | 3.35 | 3.47 | 3.93 | 3.53 | 3.51 | 3.38 | 2.90 | 2.98 | 2.89 | 2.78 | 2.70 | 2.70 |
| 14 | Mean | 78.76 | 77.91 | 77.24 | 76.82 | 76.70 | 76.06 | 75.73 | 75.36 | 75.33 | 75.21 | 75.21 | 75.18 | 75.09 |
|   | Std  | 3.89 | 4.45 | 3.91 | 3.90 | 4.04 | 3.54 | 3.60 | 3.29 | 3.31 | 3.29 | 3.29 | 3.24 | 3.06 |
| 18 | Mean | 78.58 | 77.64 | 76.48 | 75.85 | 75.73 | 75.52 | 75.39 | 74.88 | 75.06 | 74.94 | 75.03 | 74.94 | 74.82 |
|   | Std  | 4.25 | 4.11 | 3.98 | 3.63 | 3.62 | 3.73 | 3.64 | 3.40 | 3.31 | 3.15 | 3.13 | 3.08 | 3.15 |
| 22 | Mean | 78.48 | 78.15 | 77.36 | 77.00 | 76.52 | 76.09 | 75.85 | 75.36 | 75.27 | 75.27 | 75.15 | 75.18 | 75.00 |
|   | Std  | 4.68 | 4.55 | 4.03 | 3.96 | 3.97 | 3.57 | 3.85 | 3.55 | 3.56 | 3.56 | 3.46 | 3.48 | 3.43 |
| 26 | Mean | 78.97 | 77.94 | 76.61 | 76.45 | 76.12 | 75.58 | 75.45 | 75.18 | 74.97 | 74.88 | 74.67 | 74.82 | 74.64 |
|   | Std  | 3.59 | 3.69 | 4.15 | 3.98 | 3.85 | 3.35 | 3.60 | 3.50 | 3.40 | 3.30 | 3.18 | 3.12 | 3.10 |
| 30 | Mean | 79.67 | 78.61 | 77.85 | 77.00 | 76.45 | 76.33 | 76.00 | 75.82 | 75.61 | 75.58 | 75.45 | 75.39 | 75.21 |
|   | Std  | 4.54 | 3.69 | 3.99 | 4.10 | 3.56 | 3.15 | 3.30 | 3.37 | 3.24 | 3.25 | 3.33 | 3.30 | 3.45 |
| 35 | Mean | 78.55 | 77.64 | 76.55 | 76.52 | 75.97 | 75.48 | 75.18 | 75.24 | 75.21 | 75.24 | 75.18 | 75.15 | 75.06 |
|   | Std  | 4.42 | 3.87 | 3.60 | 3.93 | 3.53 | 3.31 | 3.41 | 3.55 | 3.67 | 3.46 | 3.25 | 3.14 | 2.97 |
| 40 | Mean | 78.55 | 77.33 | 76.61 | 75.94 | 75.09 | 74.91 | 74.82 | 74.76 | 74.76 | 74.79 | 74.73 | 74.67 | 74.48 |
|   | Std  | 4.15 | 4.49 | 3.74 | 4.00 | 3.48 | 3.17 | 3.30 | 3.26 | 3.18 | 3.16 | 3.05 | 2.98 | 2.96 |
| 45 | Mean | 79.42 | 78.21 | 77.82 | 77.36 | 76.67 | 76.12 | 75.70 | 75.64 | 75.61 | 75.42 | 75.42 | 75.45 | 75.42 |
|   | Std  | 4.65 | 4.34 | 4.27 | 4.32 | 3.81 | 3.63 | 3.57 | 3.35 | 3.34 | 2.99 | 3.02 | 3.08 | 3.14 |
| 50 | Mean | 79.18 | 78.94 | 77.97 | 77.06 | 76.55 | 75.97 | 75.64 | 75.52 | 75.33 | 75.18 | 74.85 | 74.82 | 74.91 |
|   | Std  | 4.32 | 3.76 | 3.87 | 3.71 | 3.65 | 3.09 | 2.93 | 3.13 | 3.31 | 3.14 | 3.03 | 3.04 | 3.08 |

Values shown in Table 4 are per each $N_h$ and $N_{ep}$ pair for an MLP with 30 inputs, these 30 inputs are derived from the 3 textural features selected and the 10 NGLCMs as trained and tested for the exemplary FLS system, described above. After examining all potential testing accuracies for the $N_h$ and $N_{ep}$ pairs in Table 4, $N_h$=45 with $N_{ep}$=200 were chosen for subsequent training and testing at 1000 Monte Carlo runs.

Table 5 shows the results of the average performance using 17 selected inputs to the MLP network, these 17 inputs are also drawn from the 198 clips, nine features and 10 GLCMs described above.

TABLE 5

Testing Accuracy mean and standard deviation (std) for 50-run Monte-Carlo Simulation

| Validation | | Number of Training Epochs $N_{ep}$ | | | | | | | | | | | |
|---|---|---|---|---|---|---|---|---|---|---|---|---|---|
| $N_h$ | Accuracy | 200 | 600 | 1000 | 1400 | 1800 | 2200 | 2600 | 3000 | 3400 | 3800 | 4200 | 4600 | 5000 |
| 2 | Mean | 81.94 | 86.88 | 87.70 | 88.24 | 88.18 | 88.30 | 88.46 | 88.58 | 88.42 | 88.39 | 88.46 | 88.33 | 88.42 |
|   | Std  | 5.77 | 4.54 | 3.92 | 4.00 | 4.25 | 4.52 | 4.32 | 4.48 | 4.69 | 4.75 | 4.56 | 4.60 | 4.58 |

TABLE 5-continued

Testing Accuracy mean and standard deviation (std) for 50-run Monte-Carlo Simulation

| | Validation | Number of Training Epochs $N_{ep}$ | | | | | | | | | | | | |
|---|---|---|---|---|---|---|---|---|---|---|---|---|---|---|
| $N_h$ | Accuracy | 200 | 600 | 1000 | 1400 | 1800 | 2200 | 2600 | 3000 | 3400 | 3800 | 4200 | 4600 | 5000 |
| 4 | Mean | 81.82 | 85.03 | 87.42 | 87.52 | 87.79 | 87.73 | 87.67 | 87.79 | 87.88 | 87.94 | 87.64 | 87.76 | 87.82 |
| | Std | 6.41 | 6.72 | 4.44 | 3.87 | 4.16 | 4.40 | 4.54 | 4.74 | 4.85 | 4.65 | 4.89 | 4.68 | 4.75 |
| 6 | Mean | 80.24 | 84.73 | 86.36 | 86.79 | 87.09 | 87.67 | 87.73 | 87.91 | 88.33 | 88.18 | 87.97 | 88.00 | 88.03 |
| | Std | 5.24 | 4.25 | 4.47 | 4.47 | 4.64 | 4.16 | 4.24 | 4.19 | 4.19 | 4.29 | 4.27 | 4.42 | 4.62 |
| 8 | Mean | 81.06 | 84.97 | 86.48 | 88.00 | 87.94 | 89.09 | 89.30 | 89.30 | 89.33 | 89.27 | 89.39 | 89.39 | 89.30 |
| | Std | 8.52 | 7.06 | 7.05 | 7.01 | 7.35 | 4.37 | 4.34 | 4.20 | 4.15 | 4.28 | 4.27 | 4.46 | 4.46 |
| 10 | Mean | 80.27 | 85.33 | 87.88 | 88.73 | 88.76 | 88.36 | 88.76 | 88.73 | 88.70 | 88.85 | 88.73 | 89.21 | 89.21 |
| | Std | 8.66 | 5.14 | 4.49 | 4.09 | 4.02 | 3.96 | 3.90 | 4.14 | 4.24 | 4.10 | 4.21 | 3.89 | 4.33 |
| 14 | Mean | 79.36 | 85.85 | 88.15 | 89.09 | 89.94 | 90.48 | 90.39 | 90.79 | 90.73 | 91.18 | 90.94 | 91.24 | 91.33 |
| | Std | 9.81 | 6.92 | 5.57 | 4.60 | 4.56 | 3.67 | 4.19 | 3.83 | 3.96 | 3.96 | 3.83 | 3.72 | 3.91 |
| 18 | Mean | 81.52 | 86.15 | 88.15 | 89.55 | 90.03 | 90.30 | 90.52 | 90.70 | 90.82 | 90.64 | 90.64 | 90.61 | 90.64 |
| | Std | 6.36 | 5.47 | 4.08 | 4.06 | 4.34 | 4.16 | 3.76 | 3.76 | 3.72 | 3.93 | 3.87 | 3.94 | 4.06 |
| 22 | Mean | 79.82 | 84.58 | 86.48 | 87.85 | 88.61 | 88.94 | 89.15 | 88.91 | 89.30 | 89.21 | 89.55 | 89.79 | 89.85 |
| | Std | 9.88 | 4.24 | 4.68 | 4.10 | 4.21 | 3.96 | 4.44 | 4.91 | 4.65 | 4.76 | 4.79 | 4.79 | 4.77 |
| 26 | Mean | 79.48 | 85.27 | 87.88 | 89.09 | 89.76 | 90.18 | 90.79 | 90.70 | 90.55 | 90.67 | 90.64 | 90.64 | 90.52 |
| | Std | 7.78 | 6.03 | 4.97 | 5.36 | 5.23 | 4.88 | 4.58 | 4.65 | 4.86 | 5.15 | 4.93 | 5.03 | 5.04 |
| 30 | Mean | 79.91 | 85.09 | 86.94 | 87.79 | 88.61 | 89.42 | 89.55 | 89.58 | 89.58 | 89.70 | 89.67 | 89.97 | 89.82 |
| | Std | 7.48 | 5.08 | 4.78 | 4.96 | 5.32 | 5.17 | 5.10 | 5.21 | 5.35 | 5.13 | 5.05 | 4.91 | 4.85 |
| 35 | Mean | 80.00 | 84.30 | 85.36 | 86.27 | 87.12 | 87.58 | 88.18 | 88.39 | 88.55 | 88.61 | 88.64 | 88.73 | 88.55 |
| | Std | 6.33 | 4.99 | 5.12 | 5.17 | 5.10 | 4.95 | 4.87 | 4.94 | 4.73 | 4.66 | 4.85 | 4.60 | 4.76 |
| 40 | Mean | 79.24 | 84.58 | 86.79 | 87.85 | 89.03 | 89.36 | 89.79 | 89.82 | 90.06 | 89.97 | 89.91 | 89.94 | 90.15 |
| | Std | 10.07 | 6.37 | 5.45 | 5.63 | 4.96 | 4.88 | 4.82 | 5.05 | 4.52 | 4.62 | 4.91 | 5.04 | 4.77 |
| 45 | Mean | 80.39 | 85.88 | 87.61 | 88.48 | 89.27 | 89.73 | 89.85 | 90.27 | 90.39 | 90.30 | 90.42 | 90.36 | 90.45 |
| | Std | 8.30 | 3.95 | 4.07 | 4.37 | 3.86 | 3.84 | 3.93 | 3.93 | 4.06 | 4.08 | 3.97 | 3.93 | 4.02 |
| 50 | Mean | 78.06 | 84.09 | 86.36 | 87.52 | 88.94 | 89.73 | 90.03 | 90.09 | 90.09 | 89.97 | 90.15 | 90.30 | 90.18 |
| | Std | 9.93 | 7.95 | 7.73 | 7.98 | 5.44 | 5.32 | 5.42 | 5.30 | 5.05 | 4.96 | 5.08 | 4.99 | 5.32 |

After examining all promising $N_h$ and $N_{ep}$ pairs in Table 5, $N_h=8$ with $N_{ep}=1800$ were chosen for the 1000 Monte Carlo run.

A summary of sensitivity, specificity, and accuracy for the training set and testing set in the example of 198 clips for the MLP systems using three textural features of the FLS system, 30 inputs, and using 17 selected features as described above, are provided in Tables 6 and 7, respectively.

The testing sensitivity, specificity and accuracy for the 17 selected features is improved over either the 30 input MLP system or the FLS system.

In yet another embodiment, 90 inputs were used to train and test an MLP system as described above. The 90 inputs were obtained from the 10 GLCMs, normalized, and all nine textural features calculated from the GLCMs, all originating from the 198 clips. After examining all potentially promising $N_h$ and $N_{ep}$ pairs in Table 3.12 that yielded the best validation accuracy, $N_h=8$ with $N_{ep}=1800$ were chosen. The results are provided below.

TABLE 6

Sensitivity, specificity and accuracy mean and standard deviation (std) for training and testing sets after 1000-run Monte-Carlo simulation for a MLP of 30 inputs

| | Training | | | Testing | | |
|---|---|---|---|---|---|---|
| | Sensitivity (%) | Specificity (%) | Accuracy (%) | Sensitivity (%) | Specificity (%) | Accuracy (%) |
| Mean ± std | 81.91 ± 5.76 | 68.09 ± 4.86 | 75.70 ± 3.11 | 82.10 ± 7.92 | 67.93 ± 8.03 | 75.14 ± 3.28 |

TABLE 7

Sensitivity, specificity and accuracy mean and standard deviation (std) for training and testing sets after 1000-run Monte-Carlo simulation for a MLP of 17 inputs

| | Training | | | Testing | | |
|---|---|---|---|---|---|---|
| | Sensitivity (%) | Specificity (%) | Accuracy (%) | Sensitivity (%) | Specificity (%) | Accuracy (%) |
| Mean ± std | 99.00 ± 1.84 | 93.41 ± 6.67 | 96.42 ± 3.50 | 94.42 ± 4.71 | 85.40 ± 8.49 | 90.16 ± 4.57 |

TABLE 8

Sensitivity, specificity and accuracy mean and standard deviation (std) for
training and testing sets after 1000-run Monte-Carlo simulation
for a MLP of 90 inputs

| | Training | | | Testing | | |
|---|---|---|---|---|---|---|
| | Sensitivity (%) | Specificity (%) | Accuracy (%) | Sensitivity (%) | Specificity (%) | Accuracy (%) |
| Mean ± std | 97.06 ± 6.58 | 90.39 ± 5.93 | 93.96 ± 4.29 | 90.67 ± 8.29 | 81.42 ± 8.15 | 86.36 ± 5.46 |

As such, images derived from clips, such as those represented in FIGS. 3 and 5 may be evaluated for signal patterning. Images depicting variations in power distribution (non-uniformity) may be further focused. For example, images of FIG. 3 were focused to a low frequency range. One or more encoding schemes that rely on contrast level encoding are used to further enhance the distribution of signal recordings in the image. In one example, four different grey-scale shadings were used to represent each point in the plot. The encodings are translated into differences in one or more extracted textural features. The textural features selection method employs a first degree statistical analysis yielding features that are sufficient to produce useful, quantitative results which compare well with current qualitative analyses. Detection rates may also rely on alternative techniques than those described, for example, the MLP system described herein.

A method of processing, analyzing and training a fuzzy logic system or an MLP system to classify signals as between two classes is readily apparent from the detailed description above. Beginning with EKG signals from known classes, a fuzzy logic system or an MLP system can be trained to classify unknown records into the two known classes. Examples of classes include: normal signals and congestive heart failure signals; normal and long Q-T interval signals; or normal signals and OSH. A key step in the signal processing from which textural features are extracted is the calculation of GLCMs from STDFT matrices.

Not all people with suspected sleep apnea require medical tests. Expensive diagnostic efforts are probably not required for individuals who have no other health risk factors and whose suspected apnea does not affect their quality of life or safety on the road. However, patients with impaired lifestyles and other medical complications need to be screened for sleep apnea. Non-invasive, minimally intrusive, methods of detecting sleep apnea are needed. The present invention provides a method for such diagnosis.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A method of developing a sleep disorder detection system, the method comprising:
    obtaining EKG recordings from known normal patients and known sleep disorder patients;
    clipping the EKG measurements into specific time intervals, forming clips;
    calculating an R-R interval discrete time series for each clip, and evenly resampling the R-R interval discrete time series using cubic spline interpolation, creating data clips;
    performing Short-Time Discrete Fourier Transform (STDFT) on each data clip, which generates STDFT complex matrices;
    encoding each STDFT matrix into at least one grey-level image and calculating at least one Grey-Level Co-occurrence Matrix (GLCM) for each at least one grey-level image;
    calculating textural features for each GLCM;
    performing statistical analysis on each textural feature between GLCMs from known normal patients and GLCMs from known sleep disorder patients;
    formulating fuzzy logic rules based on the statistical analysis; and
    employing fuzzy logic to implement the rules and training the sleep disorder detection system using the textural features from known normal and known sleep disorder patients as inputs.

2. The method according to claim 1, wherein
at least two different grey-scale encoding methods are used to form at least two images.

3. The method according to claim 1, wherein
STDFT matrices are encoded into color images.

4. The method according to claim 1, wherein
at least two GLCMs are calculated for each image.

5. The method according to claim 1, further comprising:
segmenting encoded images into at least four equal squares or rectangles.

6. The method according to claim 5, further comprising:
calculating at least two GLCMs for each segment.

7. The method according to claim 6, wherein the at least two GLCMs for each segment, each have a different orientation ($\Theta$) parameter.

8. The method according to claim 6, wherein the at least two GLCMs for each segment, each have a different distance parameter.

9. The method according to claim 1, further comprising:
using four different grey-scale encoding methods are used to form respective four images for each STDFT matrix.

10. The method according to claim 9, further comprising:
segmenting each image into at least four equal segments;
calculating at least two different GLCMs for each segment, for at least four segments.

11. A method of screening a patient for sleep apneic episodes, the method comprising: recording nocturnal EKG signals from the patient;
    clipping the EKG measurement into specific time intervals, forming clips;
    calculating an R-R interval discrete time series for each clip, and evenly resampling the R-R interval discrete time series using cubic spline interpolation, creating data clips;
    performing Short-Time Discrete Fourier Transform (STDFT) on each data clip, which generates STDFT complex matrices;

encoding each STDFT matrix into at least one grey-level image and calculating at least one Grey-Level Co-occurrence Matrix (GLCM) for each at least one grey-level image;

calculating textural features for each GLCM;

inputting the textural features from the patient into a trained fuzzy logic system;

and identifying a sleep apneic episode for a non-normal result.

12. A method of classifying a patient as normal or as having obstructive sleep apnea, the method comprising:

using a fuzzy logic system trained to classify clips as normal or as obstructive sleep apneic;

recording nocturnal EKG signals from the patient;

clipping the EKG measurement into specific time intervals, forming clips;

calculating an R-R interval discrete time series for each clip, and evenly resampling the R-R interval discrete time series using cubic spline interpolation, creating data clips;

performing Short-Time Discrete Fourier Transform (STDFT) on each data clip, which generates STDFT complex matrices;

encoding each STDFT matrix into at least one grey-level image and calculating at least one Grey-Level Co-occurrence Matrix (GLCM) for each at least one grey-level image;

calculating textural features for each GLCM;

inputting the textural features from the patient into the trained fuzzy logic system; and classifying the patient based on the defuzzified result.

13. A computer program stored on a non-transitory computer readable medium, which when executed performs a method, the method comprising:

reading EKG recording from known normal patients and known sleep disorder patients;

clipping the EKG measurements into specific time intervals, forming clips;

calculating an R-R interval discrete time series for each clip, and evenly resampling the R-R interval discrete time series using cubic spline interpolation, creating data clips;

performing Short-Time Discrete Fourier Transform (STDFT) on each data clip, which generates STDFT complex matrices;

encoding each STDFT matrix into at least one grey-level image and calculating at least one Grey-Level Co-occurrence Matrix (GLCM) for each at least one grey-level image;

calculating textural features for each GLCM;

performing statistical analysis on each textural feature between GLCMs from known normal patients and GLCMs from known sleep disorder patients;

formulating fuzzy logic rules based on the statistical analysis; and employing fuzzy logic to implement the rules and training the sleep disorder detection system using the textural features from known normal and known sleep disorder patients as inputs.

14. The computer program of claim 13 stored on a computer readable medium, which when executed performs a method, wherein at least two different grey-scale encoding methods are used to form at least two images.

15. The computer program of claim 13 stored on a computer readable medium, which when executed performs a method, wherein at least two GLCMs are calculated for each image.

16. The computer program of claim 13 stored on a computer readable medium, which when executed performs a method, the method further comprising:

segmenting encoded images into at least four equal squares or rectangles.

17. The computer program of claim 16 stored on a computer readable medium, which when executed performs a method, the method further comprising:

calculating at least two GLCMs for each segment.

18. The computer program of claim 16 stored on a computer readable medium, which when executed performs a method, wherein the at least two GLCMs for each segment, each have at least one of a different orientation ($\Theta$) parameter or a different distance parameter.

19. The computer program of claim 13 stored on a computer readable medium, which when executed performs a method, the method further comprising:

using four different grey-scale encoding methods to form four images for each STDFT matrix.

20. A computer program stored on a non-transitory computer readable medium, which when executed performs a method, the method comprising:

recording nocturnal EKG signals from the patient;

clipping the EKG measurement into specific time intervals, forming clips;

calculating an R-R interval discrete time series for each clip, and evenly resampling the R-R interval discrete time series using cubic spline interpolation, creating data clips;

performing Short-Time Discrete Fourier Transforms (STDFT) on each data clip, which generates STDFT complex matrices;

encoding each STDFT matrix into at least one grey-level image and calculating at least one Grey-level Co-occurrence Matrix (GLCM) for each at least one grey-level image;

calculating textural features for each GLCM;

inputting the textural features from the patient into a trained fuzzy logic system;

and identifying a sleep apneic episode for a non-normal result.

* * * * *

UNITED STATES PATENT AND TRADEMARK OFFICE
CERTIFICATE OF CORRECTION

| | | |
|---|---|---|
| PATENT NO. | : 7,966,061 B2 | Page 1 of 1 |
| APPLICATION NO. | : 11/846919 | |
| DATED | : June 21, 2011 | |
| INVENTOR(S) | : Mohammad A. Al-Abed et al. | |

It is certified that error appears in the above-identified patent and that said Letters Patent is hereby corrected as shown below:

IN THE CLAIMS:

In claim 9, column 16, line 50, delete "are used".

In claim 9, column 16, line 51, delete "respective".

Signed and Sealed this
Thirtieth Day of August, 2011

David J. Kappos
*Director of the United States Patent and Trademark Office*